(12) United States Patent
Seward (10) Patent No.: US 6,398,736 B1
(45) Date of Patent: Jun. 4, 2002

(54) PARAMETRIC IMAGING ULTRASOUND CATHETER

(75) Inventor: James B. Seward, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/421,712

(22) Filed: Oct. 20, 1999

Related U.S. Application Data
(60) Provisional application No. 60/127,017, filed on Mar. 31, 1999.

(51) Int. Cl.[7] .................................................. A61B 8/14
(52) U.S. Cl. ......................... 600/466; 600/467; 128/916
(58) Field of Search ................................. 600/437, 438, 600/443, 447, 467, 462, 463, 466, 485, 306, 309; 607/27–29, 122; 128/916

(56) References Cited

U.S. PATENT DOCUMENTS

| | | |
|---|---|---|
| 3,789,833 A | 2/1974 | Bom |
| 3,817,089 A | 6/1974 | Eggleton et al. |
| 3,938,502 A | 2/1976 | Bom |
| 4,028,934 A | 6/1977 | Sollish |
| 4,110,723 A | 8/1978 | Hetz et al. |

(List continued on next page.)

FOREIGN PATENT DOCUMENTS

| | | |
|---|---|---|
| DE | 44 23 808 | 7/1994 |
| EP | 0 234 951 | 9/1987 |
| EP | 0 600 568 A1 | 6/1994 |
| EP | 0 642 762 A2 | 3/1995 |
| WO | WO 90/13260 | 11/1990 |
| WO | WO 91/04707 | 4/1991 |

(List continued on next page.)

OTHER PUBLICATIONS

Belohlavek, M. et al., "Three– and Four–Dimensional Cardiovascular Ultrasound Imaging: A New Era for Echocardiography", *Mayo Clin Proc.*, 68:221–240 (Mar. 1993).

Belohlavek, M. et al., "Toroidal Geometry: Novel Three–Dimensional Intracardiac Imaging with a Phased–Array Transducer", *Journal Am. Soc. of Echocardiography*, 10(5):493–498 (Jun. 1997).

(List continued on next page.)

*Primary Examiner*—Marvin M. Lateef
*Assistant Examiner*—Ali M. Imam
(74) *Attorney, Agent, or Firm*—Merchant & Gould P.C.

(57) ABSTRACT

A parametric imaging ultrasound catheter apparatus is capable of obtaining parametric images of the surrounding insonated environment. Parametric imaging is defined as the imaging of quantifiable "parameters" which of visible two-, three-, fourth-dimensional or non-visible higher-dimensional temporal physiologic events. Visible motion is a fourth-dimensional event and includes surrogate features of cardiac muscle contraction, wall motion, valve leaflet motion, etc. Non-visible motion is a higher-dimensional event and includes slow non-visible events (i.e., remodeling, transformation, aging, healing, etc.) or fast non-visible events (i.e., heat, electricity, strain, compliance, perfusion, etc.). An ultrasound catheter with parametric imaging capability can obtain dynamic digital or digitized information from the surrounding environment and display information features or quanta as a static or dynamic geometric figures from which discrete or gross quantifiable information can be obtained. A quantifiable geometric image or parametric information may have little resemblance or dependence on the fundamental ultrasound image. Parametric ultrasound information may be used as a surrogate for common visible or non-visible events such as electrical depolarization of the heart, perfusion, myocardial injury, etc.

12 Claims, 7 Drawing Sheets

U.S. PATENT DOCUMENTS

| | | |
|---|---|---|
| 4,354,502 A * | 10/1982 | Colley et al. ............... 600/467 |
| 4,374,525 A | 2/1983 | Baba |
| 4,391,282 A | 7/1983 | Ando et al. |
| 4,462,408 A | 7/1984 | Silverstein et al. |
| 4,466,444 A | 8/1984 | Baba |
| 4,543,960 A | 10/1985 | Harui et al. |
| 4,550,607 A | 11/1985 | Maslak et al. |
| 4,582,067 A | 4/1986 | Silverstein et al. |
| 4,699,009 A | 10/1987 | Maslak et al. |
| 4,748,985 A | 6/1988 | Nagasaki |
| 4,756,313 A | 7/1988 | Terwilliger |
| 4,757,821 A | 7/1988 | Snyder |
| 4,771,788 A | 9/1988 | Millar |
| 4,794,931 A | 1/1989 | Yock |
| 4,802,487 A | 2/1989 | Martin et al. |
| 4,841,977 A | 6/1989 | Griffith et al. |
| 4,841,979 A | 6/1989 | Dow et al. |
| 4,869,256 A | 9/1989 | Kanno et al. |
| 4,869,258 A | 9/1989 | Hetz |
| 4,887,605 A | 12/1989 | Angelsen et al. |
| 4,911,170 A | 3/1990 | Thomas, III et al. |
| 4,917,097 A | 4/1990 | Proudian et al. |
| 4,930,515 A | 6/1990 | Terwilliger |
| 4,936,281 A | 6/1990 | Stasz |
| 4,947,852 A | 8/1990 | Nassi et al. |
| 4,951,677 A | 8/1990 | Crowley et al. |
| 4,957,111 A | 9/1990 | Millar |
| 5,000,185 A | 3/1991 | Yock |
| 5,002,059 A | 3/1991 | Crowley, et al. |
| 5,010,886 A | 4/1991 | Passafaro et al. |
| 5,014,710 A | 5/1991 | Maslak et al. |
| 5,022,399 A | 6/1991 | Biegeleisen |
| 5,029,588 A | 7/1991 | Yock et al. |
| 5,038,789 A | 8/1991 | Frazin |
| 5,070,879 A | 12/1991 | Herres |
| 5,076,278 A | 12/1991 | Vilkomerson et al. |
| 5,076,279 A | 12/1991 | Arenson et al. |
| 5,081,993 A | 1/1992 | Kitney et al. |
| 5,085,221 A | 2/1992 | Ingebritsen et al. |
| 5,105,819 A | 4/1992 | Wollschläger et al. |
| 5,107,844 A | 4/1992 | Kami et al. |
| 5,115,814 A | 5/1992 | Griffith et al. |
| 5,125,410 A | 6/1992 | Misono et al. |
| 5,135,001 A | 8/1992 | Sinofsky et al. |
| 5,140,558 A | 8/1992 | Harrison, Jr. et al. |
| 5,148,810 A | 9/1992 | Maslak et al. |
| 5,152,294 A | 10/1992 | Mochizuki et al. |
| 5,159,931 A | 11/1992 | Pini |
| 5,161,537 A | 11/1992 | Hashimoto et al. |
| 5,165,413 A | 11/1992 | Maslak et al. |
| 5,174,296 A | 12/1992 | Watanabe et al. |
| 5,181,514 A | 1/1993 | Solomon et al. |
| 5,183,048 A | 2/1993 | Eberle |
| 5,186,175 A | 2/1993 | Hirama et al. |
| 5,186,177 A | 2/1993 | O'Donnell et al. |
| 5,193,546 A | 3/1993 | Shaknovich |
| 5,199,433 A | 4/1993 | Metzger et al. |
| 5,199,437 A | 4/1993 | Langberg |
| 5,211,168 A | 5/1993 | Mason et al. |
| 5,215,092 A | 6/1993 | Wray |
| 5,222,501 A | 6/1993 | Ideker et al. |
| 5,226,422 A | 7/1993 | McKeighen et al. |
| 5,235,986 A | 8/1993 | Maslak et al. |
| 5,243,988 A | 9/1993 | Sieben et al. |
| 5,257,629 A | 11/1993 | Kitney et al. |
| 5,261,408 A | 11/1993 | Maslak et al. |
| 5,285,788 A | 2/1994 | Arenson et al. |
| 5,291,893 A | 3/1994 | Slayton |
| 5,295,486 A | 3/1994 | Wollschläger et al. |
| 5,297,553 A | 3/1994 | Sliwa, Jr. et al. |
| 5,299,578 A | 4/1994 | Rotteveel et al. |
| 5,305,755 A | 4/1994 | Nakao |
| 5,305,756 A | 4/1994 | Entrekin et al. |
| 5,311,871 A | 5/1994 | Yock |
| 5,313,949 A | 5/1994 | Yock |
| 5,320,104 A | 6/1994 | Fearnside et al. |
| 5,325,860 A | 7/1994 | Seward et al. |
| 5,329,496 A | 7/1994 | Smith |
| 5,329,927 A | 7/1994 | Gardineer et al. |
| 5,343,865 A | 9/1994 | Gardineer et al. |
| 5,345,940 A | 9/1994 | Seward et al. |
| 5,351,691 A | 10/1994 | Brommersma |
| 5,360,007 A | 11/1994 | Shinomura et al. |
| 5,373,845 A | 12/1994 | Gardineer et al. |
| 5,373,849 A | 12/1994 | Maroney et al. |
| 5,377,685 A | 1/1995 | Kazi et al. |
| 5,385,148 A | 1/1995 | Lesh et al. |
| 5,398,689 A | 3/1995 | Connor et al. |
| 5,402,793 A | 4/1995 | Gruner et al. |
| 5,415,175 A | 5/1995 | Hanafy et al. |
| 5,421,336 A | 6/1995 | De Bernardis |
| 5,425,370 A | 6/1995 | Vilkomerson |
| 5,437,283 A | 8/1995 | Ranalletta et al. |
| 5,438,997 A | 8/1995 | Sieben et al. |
| 5,438,998 A | 8/1995 | Hanafy |
| 5,460,181 A | 10/1995 | Seyed-Bolorforosh |
| 5,464,016 A | 11/1995 | Nicholas et al. |
| 5,465,724 A | 11/1995 | Sliwa, Jr. et al. |
| 5,467,779 A | 11/1995 | Smith et al. |
| 5,469,852 A | 11/1995 | Nakamura et al. |
| 5,474,075 A | 12/1995 | Goldberg et al. |
| 5,479,929 A | 1/1996 | Cooper et al. |
| 5,479,930 A | 1/1996 | Gruner et al. |
| 5,485,846 A | 1/1996 | Webler et al. |
| 5,487,388 A | 1/1996 | Rello et al. |
| 5,499,630 A | 3/1996 | Hiki et al. |
| 5,503,152 A | 4/1996 | Oakley et al. |
| 5,549,111 A | 8/1996 | Wright et al. |
| 5,562,095 A | 10/1996 | Downey et al. |
| 5,569,276 A | 10/1996 | Jang et al. |
| 5,630,416 A | 5/1997 | Urchikura et al. |
| 5,634,464 A | 6/1997 | Jang et al. |
| 5,697,377 A | 12/1997 | Wittkampf |
| 5,699,805 A | 12/1997 | Seward et al. |
| 5,704,361 A | 1/1998 | Seward et al. |
| 5,713,363 A | 2/1998 | Seward et al. |
| 5,749,833 A | 5/1998 | Hakki et al. |
| 5,876,345 A | 3/1999 | Eaton et al. |
| 5,904,651 A | 5/1999 | Swanson et al. |
| 5,957,846 A * | 9/1999 | Chiang et al. ............... 600/447 |

FOREIGN PATENT DOCUMENTS

| | | |
|---|---|---|
| WO | WO 93/08738 | 5/1993 |
| WO | WO 94/16625 | 8/1994 |
| WO | WO 95/13111 | 5/1995 |
| WO | WO 95/19143 | 7/1995 |
| WO | WO 96/00522 | 1/1996 |
| WO | WO 96/03918 | 2/1996 |
| WO | WO 96/03921 | 2/1996 |
| WO | WO 96/03922 | 2/1996 |
| WO | WO 96/04588 | 2/1996 |

OTHER PUBLICATIONS

Lam, J. et al., "Transesophageal Echocardiography with the Use of a Four–Millimeter Probe", *Journal Am. Soc. of Echocardiography*, 10(5):499–504 (Jun. 1977).

McCann, H.A. et al., "Multidimensional Ultrasonic Imaging for Cardiology", *Proc IEEE*, 76(9):1063–1071 (Sep. 1988).

Bom, N. et al., "Early and Recent Intraluminal Ultrasound Devices", *International Journal of Cardiac Imaging*, 4:79–88 (1989).

Bom, N. et al., "Intravascular Ultrasound: Newest Branch of the Echo–Tree", *Cardiovascular Imaging*, 4:55–59 (1992).

Devonald, K.J. et al., "Volume Imaging: Three–Dimensional Appreciation of the Fetal Head and Face", *J. Ultrasound Med.*, 14:919–925 (1995).

Entrekin, R. et al., "Real–Time 3–D Ultrasound Imaging with a 1–D 'Fan Beam' Transducer Array", *SPIE*, 1733:264–272 (1992).

F–D–C Reports, Inc., "Cardiovascular Imaging Systems' Intracardiac Imaging Catheter", *M–D–D–I Reports*, pp. I&W–6 and I&W–7 (Mar. 30, 1992).

Hung, J. et al., "Usefulness of Intracardiac Echocardiography in Transseptal Puncture During Percutaneous Transvenous Mitral Commissurotomy", *Section of Cardiology, Chang Gung Medical College and Chang Gung Memorial Hospital*, p. 853 (May 10, 1993).

Kossoff, G. et al., "Real–Time Quasi–Three–Dimensional Viewing in Sonography, with Conventional, Gray–Scale Volume Imaging", *Ultrasound Obstet. Gynecol.*, 4:211–216 (1994).

Kremkau, F.W., "AAPM Tutorial. Multiple–Element Transducers", *RadioGraphics*, pp. 1163–1176 (Sep. 1993).

Moriuchi, M. et al., "Transvenous Echocardiography: Experimental Feasibility Study", *Jpn J Med Ultrasonics*, 19(3)228–235 (1992).

Nishimura, R.A. et al., "Intravascular Ultrasound Imaging: In Vitro Validation and Pathologic Correlation", *JACC*, 16(1):145–154 (Jul. 1990).

Pandian, N.G. et al., "Intracardiac, Intravascular, Two–Dimensional, High–Frequency Ultrasound Imaging of Pulmonary Artery and Its Branches in Humans and Animals", *Circulation*, 81(6):2007–2012 (Jun. 1990).

Pandian, N.G. et al., "Intracardiac Echocardiography. Experimental Observations on Intracavitary Imaging of Cardiac Structures with 20–MHz Ultrasound Catheters", *Echocardiography*, 8:127–134 (Jan. 1991).

Pandian, N.G. et al., "Real–Time, Intracardiac, Two–Dimensional Echocardiography. Enhanced Depth of Field with a Low–Frequency (12.5 MHz) Ultrasound Catheter", *Echocardiography*, 8(4):407–422 (1991).

Papavasassiliou, D. et al., "Initial Experience with an Internally Rotating Transthoracic Three–Dimensional Exhocardiographic Probe and Image Acquisition on a Conventional Echocardiogram Machine", *Echocardiography: A Jrnl. of CB Ultrasound & Allied Tech.*, vol. 15, No. 4, 1998.

Rothman, A. et al., "Intraluminal Ultrasound Imaging Through a Balloon Dilation Catheter in an Animal Model of Coarctation of the Aorta", *Circulation*, 85(6):2291–2295 (Jun. 1992).

Schwartz, S. et al., "Intracardiac Echocardiographic Guidance and Monitoring During Aortic and Mitral Balloon Valvuloplasty: In Vivo Experimental Studies", Abstract, *JACC*, 15(2):104A (Feb. 1990).

Schwartz, S.L. et al., "Real–Time Intracardiac Two–Dimensional Echocardiography: An Experimental Study of In Vivo Feasibility, Imaging Planes, and Echocardiographic Anatomy", *Echocardiography*, 7(4):443–455 (Jul. 1990).

Schwartz, S.L. et al., "Intracardiac Echocardiography During Simulated Aortic and Mitral Balloon Vavuloplasty: In Vivo Experimental Studies", *Am. Heart Journal*, 123(3):665–674 (Mar. 1992).

Schwartz, S.L. et al., "Intracardiac Echocardiography in Humans Using a Small–Sized (6F), Low Frequency (12.5 MHz) Ultrasound Catheter", *JACC*, 21(1):189–198 (Jan. 1993).

Schwartz, S.L. et al., "Intracardiac Echocardiographic Imaging of Cardiac Abnormalities, Ischemic Myocardial Dysfunction, and Myocardial Perfusion: Studies With a 10 MHz Ultrasound Catheter", *Journal Am Soc. of Echocardiography*, 6(4):345–355 (Jul.–Aug. 1993).

Schwartz, S.L. et al., "Intracardiac Echocardiography Without Fluoroscopy: Potential of a Balloon–Tipped, Flow–Directed Ultrasound Catheter", *Am. Heart Journal*, 129(3):598–603 (Mar. 1995).

Seward, J.B. et al., "Transvascular and Intracardiac Two–Dimensional Echocardiography", *Echocaridography*, 7(4):457–464 (Jul. 1990).

Seward, J.B., et al., "Multiplane Transesophageal Echocardiography: Image Orientation, Examination Technique, Anatomic Correlations, and Clinical Applications", *Mayo Clin Proc.*, 68:523–551 (Jun. 1993).

Seward, J.B. et al., "Ultrasound Cardioscopy: Embarking on a New Journey", *Mayo Clin Proc.*, 71(7):629–635 (Jul. 1996).

Smith, S.W. et al., "High–Speed Ultrasound Volumetric Imaging System—Part I: Transducer Design and Beam Steering", *IEEE Transactions on Ultrasonics, Ferroelectrics, and Frequency Control*, 38(2):100–108 (Mar. 1991).

Talbert, D.G., "An 'Add–On' Modification for Linear Array Real Time Ultrasound Scanners to Produce 3 Dimensional Displays", Conference: Ultrasonics International 1977. Brighton, England, pp. 52–67 (Jun. 28–30, 1997).

Tardif, J., et al., "Intracardiac Echocardiography With a Steerable Low–Frequency Linear–Array Probe for Left–Sided Heart Imaging From the Right Side; Experimental Studies" *Journal Am. Soc. of Echocardiography*, 8(2):132–138 (Mar.–Apr. 1995).

von Ramm, O.T. et al., "High–Speed Ultrasound Volumetric Imaging System—Part II: Parallel Processing and Image Display", *IEEE Transactions on Ultrasonics, Ferroelectrics, and Frequency Control*, 38(2):109–115 (Mar. 1991).

Weintraub, A. et al., "Realtime Intracardiac Two–Dimensional Echocardiography in the Catheterization Laboratory in Humans". Abstract *JACC*, 15(2):16A (Feb. 1990).

Weintraub, A.R. et al., "Intracardiac Two–dimensional Echocardiography in Patients with Pericardial Effusion and Cardiac Tamponade", *Journal Am Soc. of Echocardiography*, 4(6):571–576 (Nov.–Dec. 1991).

* cited by examiner

PARAMETRIC IMAGING ULTRASOUND CATHETER

This Appln claims benefits of Prov. No. 60/127,017 filed Mar. 31, 1999.

FIELD OF THE INVENTION

This invention relates to a catheter apparatus, more particularly to an underfluid ultrasound parametric imaging catheter apparatus.

BACKGROUND OF THE INVENTION

Medical Ultrasound

In the field of medical ultrasound, one acquires ever more knowledge of reality by solving problems and finding better explanations. Medical ultrasound over the past 25 years has evolved to become one of the most commonly performed imaging and hemodynamic examinations. Modem ultrasound machines can replicate those features previously obtained by more invasive means such as, cardiac catheterization. Those features attributable to invasive technologies at least include: 1) ability to obtain anatomic images, 2) ability to quantitatively assess function, 3) ability to measure hemodynamics, and 4) ability to visualize blood flow (i.e., an angiographic substitute). The advantages of using ultrasound technology include: 1) non-invasive, 2) no ionizing radiation (a safe repeatable energy source), 3) comparatively low cost, 4) obtaining hemodynamics as well as images, 5) technology capable of being fabricated into different sizes and shapes (e.g., ultrasound tipped catheter), 6) rapid temporal and spatial resolution, and 7) portable, etc.

Computer Interface

With the incorporation of more sophisticated computer interfacing, in the later part of the twentieth century, diagnostic ultrasound has entered into the era of information acquisition. The prerequisites for this change include use of newer sophisticated information acquisition and management techniques, reconstruction or assimilation of multiple forms of information, segmentation of the pertinent or most meaningful information, quantitation and display of the result. The acquired information represents the physiology and structure of the insonated environment (i.e., tissue, muscle, blood, etc.). Information acquisition techniques include new Doppler technology, such as tissue Doppler imaging (TDI) and strain-rate imaging (SRI), harmonic imaging, pulse-inversion imaging, and pulsed and intermittent imaging, etc.

Ultrasound Catheter

A recent innovation in diagnostic medical ultrasound is the development and introduction of invasive ultrasound tipped catheters including (U.S. Pat. Nos. 5,325,860, 5,345, 940 and 5,713,363 issued to Seward et al.). These catheters allow one to obtain high-resolution images from within the confines of fluid filled spaces (i.e., heart, urinary bladder, blood vessels, etc.). However, these newest catheters have the capacity not only to obtain an image but in addition also to obtain more unique physiologic ultrasound information which to date has not been feasible using a rotating ultrasound element catheter. For example, full Doppler capabilities are now possible with the ultrasound catheter and include pulsed and continuous wave Doppler, color flow Doppler, tissue Doppler, etc. Newer evolving acquisition technologies include pulse inversion, harmonic imaging, strain-rate imaging, intermittent imaging, etc.

New Image Paradigm

Information can be fractionated into its small individual digital components, each unit is "parameterized" (i.e., has quantifiable value), and groups of related units can be expressed as a volumetric image. Parametric imaging referred herein is the term applied to the acquisition of various types of quantifiable events and in the case of ultrasound represents the display surrogates information representing anatomic, functional, hemodynamic, or physiologic events. A parameter is defined as a mathematical quantity or constant whose value varies with the circumstances. Examples include blood pressure, pulse rate, and an infinite number of other visible and non-visible events which permeate our reality. The quantifiable event can be measured and expressed as a change over time, for example a change in pressure over time, is most often graphed or charted as a graph (e.g. a pressure curve) with the magnitude of pressure on the ordinate and time on the abscissa. However, today a sophisticated imaging device can record such events throughout a field or volume of interest (i.e., a volumetric two- or three-dimensional image of the spatial distribution of the event). Fields of specific individual or group events can then be displayed as a geometric image as opposed to a graphic or one-dimensional display of a single continuous happening. The analogy is being capable of simultaneously measuring numerous similar or dissimilar individual events and instead of graphing the result, displaying the phenomena as a dynamic geometric image (instead of looking at a single bee in a hive, the action of the whole hive is assessed simultaneously).

The observed events can occur in a regular or irregular manner, distribute in a predictable or unpredictable manner, or remain constant or change randomly, etc. The events are virtually always continuous or cyclical (repetitive) but can be broken down into smaller and smaller components, which can be looked upon as quanta (i.e., elemental units) and displayed in a computer presentation as quantifiable pixels. It is the elemental unit(s), which can be pictured as changing over time (i.e., time and magnitude, such as pressure or temperature). However, the whole field of units (quanta) is best presented as a distribution of measurable units dispersed throughout a defined spatial domain (for example, the distribution of pressure throughout a cavity of the heart or temperature of the body). A parametric imager enables the presentation of quantifiable, information as a geometric picture of a continuous event. The event becomes the image while the fundamental image or source information becomes subservient or nonessential. At any moment in a temporal sequence, the event can be captured as a volume with a specific quantifiable distribution. However, when it is viewed over time, the event is displayed as a moving surface, and or volume (i.e., a two-, three-, fourth-dimensional or higher-dimensional image). Event information may include point of initiation (epicenter: for example, a very hot infected ear causing an increase in body temperature), distribution (epicenter spreading outward), moment to moment change (evolution or wave front distribution), decay (transient, periodicity, etc.), and others. In topological language, the point is called a repeller and the expanding phenomenon an attractor. An attractor, in general, is a region of space that "attracts" all nearby points as time passes. To the human senses, the imaged event may be a normally visible phenomenon such as the contracting wall of the heart, or a non-visible phenomenon (referred to as higher-dimensional events) such as the distribution of electricity, or in the case of ultrasound electricity can be pictured through a display of a parametric surrogate. The manipulation and display of data are solved by quantum mathematical concepts. The parametric image is a geometric image of a quantifiable phenomenon but not a mere picture of that phenomenon (for example: the motion of muscle contraction is visible, however, a parametric surrogate of contraction would be the display of change itself). The parametric image often does not appear similar to the fundamental event.

Quantum Mathematics Concept

Generally, all physical processes are quantum-mechanical. The quantum theory of computation is an integral part of the fundamental understanding of reality. Quantum solutions applied to information, displayed as a geometric image, provide a revolutionary mode of explanation of physical reality. The human does not accord equal significance to all our sensory impressions but is known to perceive reality best when presented as an image. Thus, given the fact that general theories about nature are best expressed in quantifiable mathematical form and that geometric images are the most mature expression of a mathematical computation, it is logical that a parametric image solution will have considerable acceptance as a pleasing as well as quantifiable diagnostic imaging solution. As the trend towards faster, more compact sophisticated computer hardware continues, the technology must become even more "quantum-mechanical", simply because quantum-mechanical effects dominate in all sufficiently small systems. The digital pixel of an image becomes a quantifiable unit (i.e., quanta) belonging to a family of events having related or meaningful characteristics. The repertoire of computations available to all existing computers is essentially the same. They differ only in their speed, memory capacity, and input-output devices. However, a "quantum computer" is a machine that uses uniquely quantum-mechanical effects, especially interference, to perform wholly new types of computation that would be impossible on earlier generations of computers. Such computational mathematics is a distinctively new way of looking and assessing nature. In the twentieth century, information was added to the evolution of modem computers, which has allowed complex information processing to be performed outside the human brain. As one enters into the twenty-first century, quantum computation is slowly being introduced which is the next step in the evolution of information presentation. Observations of ever smaller, subtler effects are driving ever more momentous conclusions about the nature of reality. Ever better explanations and predictions can successively approximate visible or non-visible events, which permeate the reality.

Physiological events can be computed as distributions of quanta (i.e., pixels of measurable information). Today, computers can provide integrated quantitative answers to certain otherwise unseen or unappreciated events. Quantum events are initially given a position and then "spread out" in a random volumetric distribution. Because of the unpredictability of the volumetric event, increasing computational resources must be used to measure and present the information. Quantum solutions are often used to make probabilistic predictions, however, many of the predictions can be used to predict a single, definite outcome (example: a geometric image of electricity or its surrogate, as described herein, can be used to very accurately localize the anatomic site of an electrical excitation of the heart muscle). Quantum solutions of complexity show that there is a lot more happening in the quantum-mechanical environment than that literally meets the eye. Quantum phenomena can be highly predictable and can foster the increasing use of computational solutions for the assessment of physiologic events.

Accordingly, there is a need for a computer driven acquisition device to acquire quantifiable events from today's state-of-the-art medical ultrasound machines, such as the ultrasound empowered catheter system as described herein, to rapidly acquire physiologic information and provide images of continuously changing volumetric (spatial) information.

SUMMARY OF THE INVENTION

To overcome the natural limitations in the art described above, and to overcome other limitations that will become apparent upon reading and understanding the present specification, the present invention provides a catheter apparatus for parametric imaging a visible fourth-dimensional or a non-visible higher-dimensional events in an underfluid environment.

Why a catheter—The present invention pertains to an ultrasound tipped catheter; however, the imaging solution described in the present invention could apply to any complex computer manipulation of acquired information. The ultrasound tip catheter described in the present invention has not accommodated a parametric solution before. The ultrasound catheters in the present invention are those capable of rapidly acquiring finite information presented as quantifiable pixels. The acquisition elements are in multiples aligned and spaced in a manner to act in concert to obtain a field of information (i.e., a symphony of events). Capable ultrasound include linear array, curved array, vector phased array, phased array, and multi-dimensional arrays. All of these ultrasound transducers are characterized by having multiple piezoelectric elements lying closely together and function to insonate a field and acquire underlying information. The resulting image can be a flat two-dimensional tomogram or a volumetric three-dimensional image.

Why ultrasound—Ultrasound imaging has to date received no appreciable parametric application. Digital solutions have been slow to evolve in ultrasound imagery, as opposed to other image solutions such as radioisotopes, X-ray, or magnetic resonance. The ultrasound catheter of the present invention is unique and without comparable technology. The unique image solution of the present invention is thus applied to an equally unique acquisition device (the catheter).

What is parametric imaging and why there is potential for confusion—The term "parametric imaging" has been used for years to apply to the general concept of using measurable information to form an image. In this general definition, one could say that any picture which has a numerical value to its contents is parametric (i.e., its component parts are parameterized). This can be further extrapolated to say that any picture which is digital, such as computerized tomography (CT), magnetic resonance (MR), isotope scans, Doppler ultrasound, etc., is parametric because some or all of the acquired information is expressed as a measurable number. The present invention herein addresses a unique parametric image solution and one that requires a higher order computer solution and is not merely displayed of pixelated digital information.

Firstly, the whole image is broken down into its smallest quantifiable components (i.e., pixels, quanta, etc.). Currently, this exists for CT, MR, isotopes, and Doppler but does not exist for the remainder of the ultrasound image, x-rays, etc., which is typically presented as analog pictures.

Secondly, the digital components (i.e., pixels) are parameterized and measurable, a feature, which exists with CT, MR, and isotope images but has only recently been possible with experimental ultrasound Doppler. The analog components of images have been "digitized" in an attempt to overcome this second requirement, however "digitization" significantly narrows the measurable features. There are numerous historical examples of digital or digitized information pictures, which can be called parametric. However, this is not sufficient for the present invention herein.

Thirdly, and most importantly for the present invention, the parameterized pixels are recognized by the computer as having unique quantifiable features. Each pixel has a unique identifiable quantity. Pixels with similar features are classified as families, distributions, or probabilities. Lastly, the classified pixel features are themselves presented as a geometric picture (i.e., the Parametric Image Solution pertaining to the present invention). "Para" refers to a substitute or replacement of reality; "metric" refers to mathematical, quantifiable; and "image" refers to a geometric picture (of a mathematically derived surrogate of reality). The resultant picture may have little similarity to the image described in the second requirement. A new parametric image is formed which itself is a picture of selected information. The selected information is normally imbedded within a fundamental image. Such a process occurs rapidly to be clinically applied. Very sophisticated computer solutions are required to handle these very large digital solutions and carry out the statistical sorting of pixel features. Such parametric solutions currently exist in some CT, MR and isotope imaging but are essentially experimental. There is no mention of this form of parametric solutions in ultrasound imagery. There is absolutely no mention of such solutions applied to an underfluid ultrasound catheter.

What makes the present invention unique—Nature and its physiologic underpinnings are complex. Complex phenomena continuously change in a linear or cyclical manner. Breaking such events down into small components and then expressing complexity as understandable geometric images are extremely informative. Such images impart new information. Most importantly, such information solutions are very reproducible, more accurate than conventional measuring tools, and are quantifiable. Important prerequisites include objectivity, reproducibility, quantitation, and multidimensional display. Although a historically familiar term, parametric image, is used, the concept disclosed is a new paradigm. The solution described herein is completely new and has never been applied to an underfluid ultrasound imaging system. Nor does the solution of the present invention have any intuitive counterpart in existing ultrasound or even in related comparable "imaging" modalities such as magnetic resonance, computerized tomography, or isotopes.

The present invention provides an imaging catheter apparatus having an acquisition device or parametric imager to interpret and present to the user a new geometric image of a selected parameter of an event acquired from an ultrasound imaging catheter apparatus. The selected parameter of an event which can be a visible fourth-dimension or non-visible higher-dimensional event is displayed in an image format which distinct from the conventional fundamental ultrasound image.

In one embodiment of the present invention, an ultrasound-based parametric imaging catheter apparatus adapted for an underfluid environment is described by way of example. Accordingly, parametric imaging is defined hereinwith in terms of a unique ultrasound image presentation and quantitation technique. Without the parametric solution, described herein, information parameters appear imbedded in the fundamental image display having no separable or unique image. With the described parametric solution, quantifiable parameters such as computed velocity, surrogate electrical phenomena, derived pressure, or other constantly changing events are separated and presented as new unique images which are more readily perceived and understood by a user. Most importantly, they are objective, reproducible, quantitative (mathematical) and multidimensional. Accordingly, an underfluid ultrasound parametric imaging catheter apparatus of the present invention is capable of visualizing quantitative physiology and altered physiological states of insonated surroundings. The parametric image is one of phenomena which are normally too fast, too slow, or too complex to be accommodated with current imaging solutions.

One embodiment of the underfluid ultrasound imaging catheter apparatus in accordance with the principles of the present invention includes: a catheter body; a transducer, disposed on the catheter body, transmitting signals to a structure proximate the transducer outside of the catheter body and receiving signals which represent an event of at least one selected parameter; a parametric image processor processing and imaging at least one selected parameter of the event. The event can be a four-dimensional event visible to a human user's eye or a higher than four-dimensional event normally non-visible to the human user's eye.

Dimensions: The subject of dimensions is complex and often confusing. Three dimensions totally explain our spatial reality, which encompass height, length and width. A volumetric image, which contains three spatial dimensions, is conventionally called a three-dimensional or volumetric image. Visible motion, as described by Einstein in 1908, is designated the fourth dimension of our reality. A volumetric image, which visibly moves, is called a four-dimensional image. Our reality is, however, permeated with an infinite number of normally non-visible moving events (the term higher-dimensional phenomenon has been applied to non-visible events, which permeate our reality but should not be confused with theoretical physics' use of the same descriptor, which refers to parallel universes or dimensions). Examples of non-visible phenomena include heat, electricity, transformation, etc. We normally perceive these events as continuous, for example, the changing temperature of the body. The non-visible events are perceived as complex, unpredictable linear or cyclical variables. In physics, complex natural events have been discussed under the headings of chaos, fractals, fuzzy logic, quantum mechanics, etc. All of these disciplines are based on the fact that immense predictability of complex systems can be obtained from less than absolute solutions. By breaking a complex event into quantifiable (i.e., parameterized) components and then presenting the event as a probability distribution in an image format is extremely enlightening. The parametric image described herein presents visible and non-visible events as geometric pictures, thus brings an otherwise complex event into our visible reality. The technique requires sophisticated computer management of information which results in extremely reproducible, quantifiable information.

Other embodiments of an underfluid ultrasound imaging catheter apparatus in accordance with the principles of the invention may include alternative or optional additional aspects. One such aspect of the present invention is that the transducer is an ultrasound-based transducer. The transducer is the catheter component which acquires information. The configuration of the transducer can be in a variety of formats. The ultrasound transducer configuration (format) can be of any form that can be accommodated into a catheter as described herein and acquire paramaterized information in a two-, three-, four-, or a higher dimensional image presentation. For example, the transducer can be a group of transducer elements or an array of transducer elements. Also, the type or operation type of the ultrasound-based transducer can be in a variety of formats. For example, the transducer can be an offset stereoscopic imaging ultrasound transducer array, a sector array, a linear array, a linear phase array, a phase linear array, a curved phase array, vector array, etc.

Another aspect of the present invention is that the selected quantifiable parameter is truly an ultrasound surrogate of a parametric phenomenon. Events such as blood flow velocity, perfusion, pressure, contractility, image features, electricity, metabolism, transformation, and a vast number of other constantly changing parameters are brought into the realm of visual reality. However, the event itself (i.e., electricity) is not visualized. Instead, ultrasound produces a surrogate parameter which can accurately predict an event such as electrical depolarization/repolarization.

Parametrics is an old term, however, in the context described herein, the application is totally different. Historically, a digital imaging system such as magnetic resonance, nuclear radioisotopes, x-ray, and computed tomography have been used to acquire pixelated information. Ultrasound has not accommodated digital solutions and in particular use of an underfluid imaging catheter is unique. The term parametric imaging has been applied in various manners but not to the ultrasound solution. The unique aspect of the present invention is the extraction of parametric information from the fundamental image and reformatting this new information into a new geometric image (i.e., parametric image).

In one aspect of the present invention, the invention is unique in that it is an underfluid catheter system with the creation of a new geometric parametric event imager.

Using an underfluid ultrasound catheter apparatus and the concept of quantum computation, one can describe families of physiologic events by geometrically expressing surrogate features. This presentation assists in explaining such events, and ultimately describing why something happens by invoking the flow of time. Quantum descriptions of distributions resolve events into measurable units of simplicity and comprehensibility and can be looked upon a high-level simplicity derived from low-level complexity. The surrogates of physiologic phenomena can be displayed as easily understood geometric images suited to the human's four-dimensional comprehension of reality.

Accordingly, the present invention provides a geometric image for an objective result of an event. Such event is reproducible. One obtains the same result each and every time if provided comparable parameters. The present invention provides a capability of placing a numerical result into a measurable scheme. Further, the present invention has a capacity to expand as a spatial distribution in surface, area, and volume.

These and various other advantages and features of novelty which characterize the invention are pointed out with particularity in the claims annexed hereto and forming a part hereof. However, for a better understanding of the invention, its advantages and objectives obtained by its use, reference should be made to the drawings which form a further part hereof, and to the accompanying descriptive matter, in which there is illustrated and described a preferred embodiment of the invention.

BRIEF DESCRIPTION OF THE DRAWINGS

A better understanding of the construction and operational characteristics of a preferred embodiment(s) can be realized from a reading of the following detailed description, especially in light of the accompanying drawings in which like reference numerals in the several views generally refer to corresponding parts.

DETAILED DESCRIPTION OF THE PREFERRED EMBODIMENTS

In the following description of the exemplary embodiment, reference is made to the accompanying drawings which form a part hereof, and in which is shown by way of illustration the specific embodiment in which the invention may be practiced. It is to be understood that other embodiments may be utilized as structural changes may be made without departing from the scope of the present invention.

The present invention provides an imaging catheter apparatus having an acquisition device (transducer and ultrasound machine) and a parametric imager which interprets and presents an acquired event of a selected parameter. The selected parameter can be a visible or non-visible quantifiable temporal event which is then displayed as a unique parametric image.

In one embodiment of the present invention, an ultrasound-based parametric imaging catheter apparatus adapted for an underfluid environment is described by way of example. Accordingly, parametric imaging is defined hereinwith as a type of ultrasound image presentation and quantitation. Without the parametric solution, parameters are presented as a part of a fundamental image and are not separated temporally or geometrically from the surroundings. With the parametric solution, parameterized information such as velocity, strain, pressure, or surrogate information representing electricity, motion, change, etc., can be recorded as constantly changing quantifiable events (pixels to volumes) and expressed as a new uniquely geometric image. As a result, even normally non-visible parameters can be more readily perceived and understood and quantified. Accordingly, an underfluid ultrasound parametric imaging catheter apparatus of the present invention is capable of quantitatively visualizing dynamic physiologic events and altered states within the insonated surroundings.

The prefix "para" of the term "parametric" refers to something which represents some naturally occurring phenomenon which may or may not look like the original. "Parametric" is defined herein as a quantifiable metric expression of a naturally occurring phenomenon. "Parametric imaging" is a geometric image of the distribution of a quantifiable phenomenon.

In one embodiment of the present invention, catheter based invasive ultrasound imaging systems, typically used for intracardiac or transvascular imaging, include transducers generally comprised of arrays of elements (e.g. linear phased array) or a single element rotated or translated to produce a tomographic field of view in an azimuthal plane. Typical arrays may include: 1) a linear array (linear sequential array), usually producing a rectangular or rhomboidal tomographic picture; 2) a cylindrical array or rotating crystal, producing a round pie-shaped tomographic cut; 3) a sector array (linear curved or vector phased array), producing a triangular shaped tomographic image. Images from these transducers are tomographic in nature and are focused both in the azimuthal and elevation planes. These transducer configurations produce a thin ultrasound cut of the insonated structures, which by nature is thin and of high resolution.

A more sophisticated catheter based ultrasound imaging solution includes transducers which obtain volumetric images. Two general techniques are utilized to obtain three-dimensional spatial information. The first utilizes the tomographic two-dimensional imaging array and fuses the information obtained from multiple spatially aligned two-dimensional images. The second technique obtains an instantaneous volumetric image with the use of two-dimensional piezoelectric element arrays (i.e., multiple rows of elements). A volumetric image obtains information in all three spatial dimensions. In summary, a parametric solution (i.e., distribution of quantifiable information) can be expanded from a conventional two-dimensional spatial domain to a three-dimensional domain. Both solutions are germane to the present invention, each having certain applications and in certain circumstances an advantage over the other.

Figure 1:
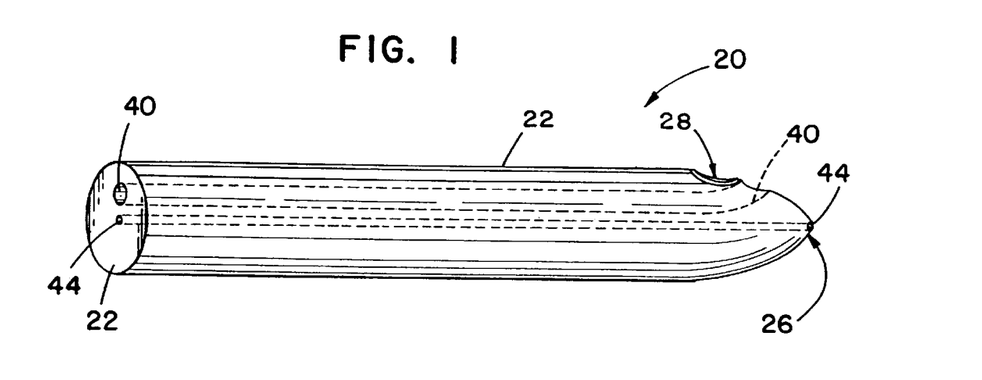
FIG. 1 is a perspective view of one embodiment of a catheter body of an underfluid ultrasound parametric imaging catheter apparatus in accordance with the principles of the present invention, in which the ultrasound catheter is an acquisition device which acquires information from the surrounding underfluid environment, and the information is processed and reformatted into a unique parametric expression of an underlying event.
Figure 2:
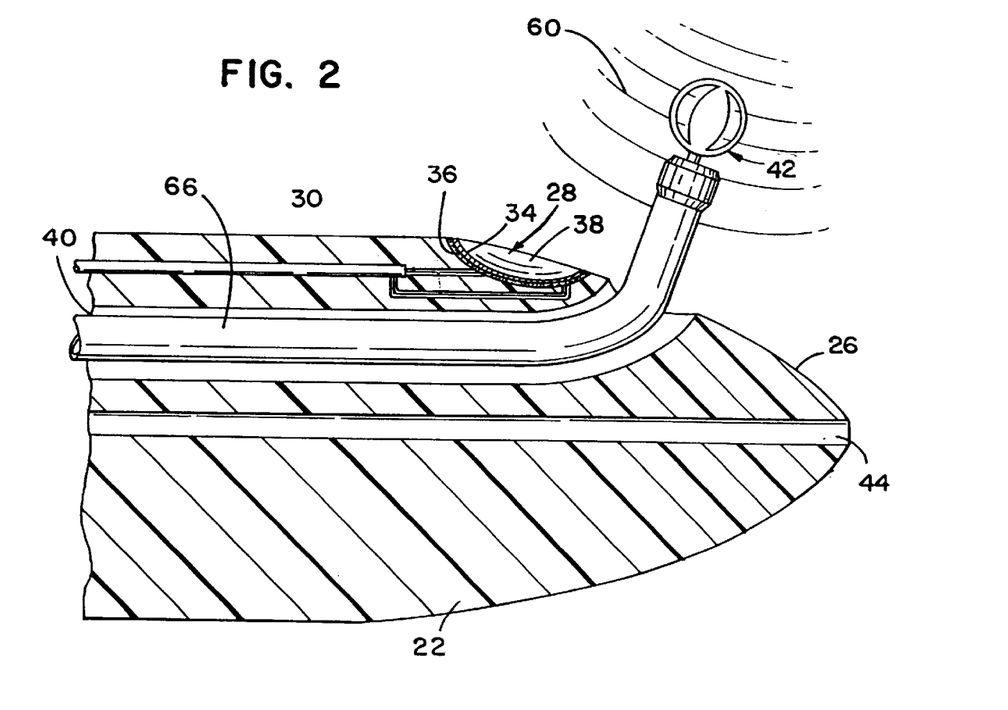
FIG. 2 is an enlarged cross-sectional view taken proximate a distal end of one embodiment of catheter body showing an ultrasonic transducer and a generic therapeutic device extending within a field of view.
Figure 3:
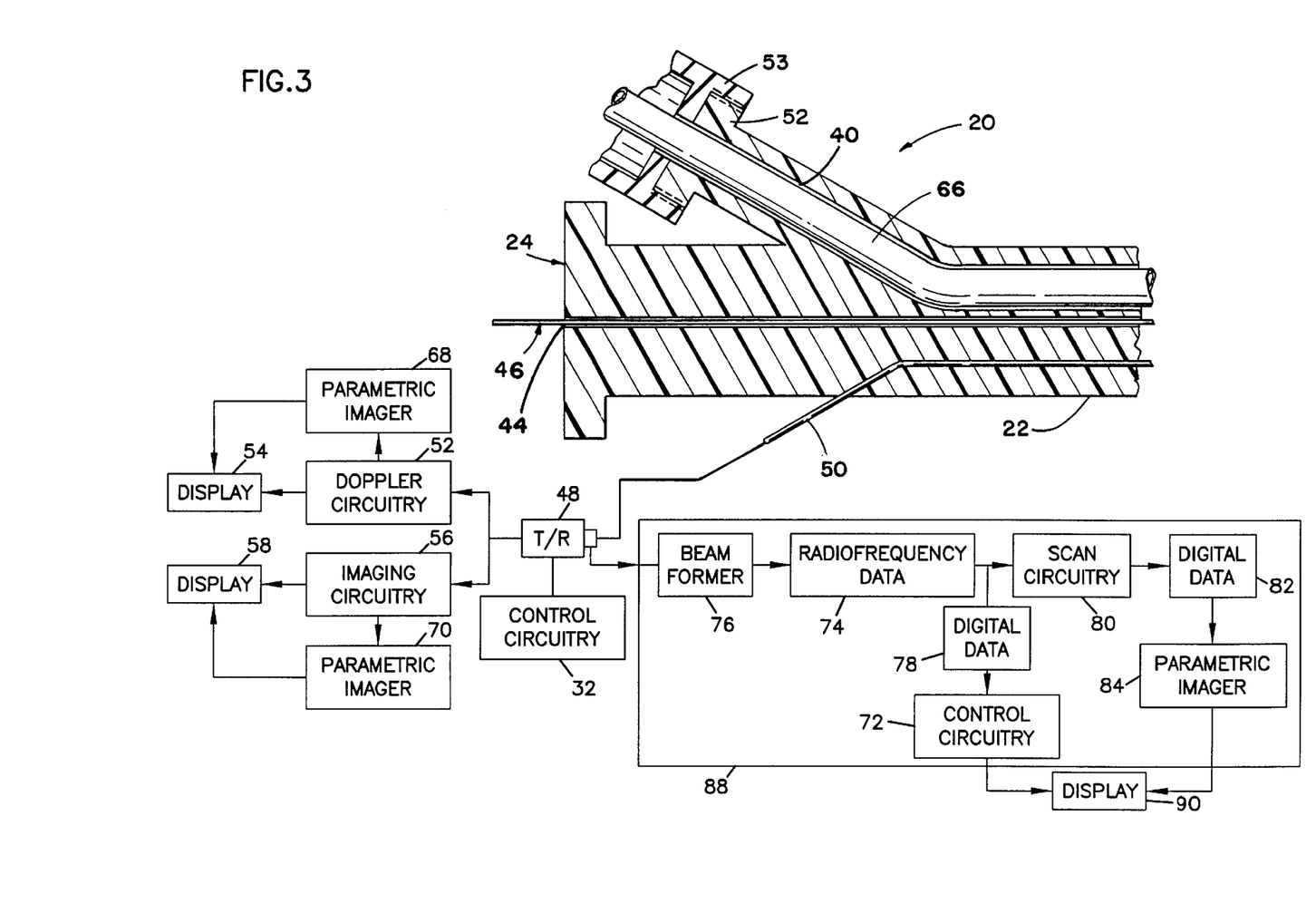
FIG. 3 is a block diagram illustrating one embodiment of the underfluid ultrasound parametric imaging catheter apparatus in accordance with the principles of the present invention.

FIGS. 1–3 illustrate one embodiment of a parametric imaging catheter apparatus in accordance with the principles of the invention. In the embodiment, an ultrasound-based catheter apparatus is generally illustrated by reference numeral 20. As shown, the catheter 20 includes an elongated flexible or rigid tubular catheter body 22 having a proximal end 24 (FIG. 3) and a distal end 26. The catheter 20 includes proximate to its longitudinal distal end 26 a phased array ultrasonic transducer 28 which is used to transmit ultrasound and receive resultant echo information such as Doppler Flow, Tissue Doppler, Color Doppler, Harmonics, Pulse Inversion, Feature Extraction or characterization, Strain, Strain Rate, Acceleration Doppler, Power Doppler, and various features. As described, various types ultrasonic transducers or transducer arrays can be used in the present invention, such as mechanical and dynamic one- and two-dimensional transducer arrays. Images can be two-dimensional or multidimensional and present tomographic, volumetric, stereoscopic, or virtual information. Various acquisition, image and display solutions are suitable for underfluid operation. The information obtained in any of these manners can be subjected to parameterization and be processed into a parametric solutions.

As shown in FIG. 2, an electrical conductor 30 is disposed in the catheter body 22 for electrically connecting the transducer 28 to a control circuitry 32 (FIG. 3) preferably external of the catheter body 22. The ultrasonic transducer 28 can be a piezoelectric material such as a ceramic crystal or polymer, such as Polyvinylidenedifloride (PVDF) 34, which is bonded by an epoxy layer 36 to a depression 38 approximate the distal end 26. Although some details are provided with respect to an embodiment of an ultrasonic transducer which might be used, it will be appreciated that various types of transducers or transducer arrays having various configurations and orientations may be utilized to obtain parametric information without departing from the principles of the present invention.

In FIGS. 1–3, additional features may be added in the catheter body 22. For example, an access port 40 may be disposed in catheter body 22. The port 40 extends from proximate the proximal end 24 of catheter body 22 to proximate the distal end 26 of catheter body 22. The port 40 may be configured to receive a therapeutic device 42, such as a catheter, medication, sensors, etc., so as to enable the device 42 to be delivered via the port 40 to the distal end 26 of the catheter body 22 for operation within the ultrasonic transducer field of view. The device 42 may be used for intervention, e.g., ablation catheter, monitoring blood pressure, and/or sampling blood, etc. Phenomena observed or so created can be subjected to the parametric information acquisition and display.

A guide wire access port 44 may also be disposed within the same catheter body 22. The port 44 extends from the proximate proximal end 24 of the catheter body 22 to proximate distal end 26 of catheter body 22 for receiving a guide wire 46 (FIG. 3).

In FIG. 3, the catheter 20 includes an appropriate control circuitry 32 for controlling operation of the ultrasonic transducer 28. The control circuitry 32 is electrically interconnected to a transceiver circuitry 48 (T/R) for transmitting and receiving signals via a cable 50 to and from the ultrasonic transducer 28. In turn, the transceiver circuitry 48 is electrically interconnected to a Doppler circuitry 52 and an appropriate display device 54 for displaying hemodynamics or blood flow, etc. In addition, the transceiver circuitry 48 is electrically interconnected to a suitable imaging circuitry 56 which is interconnected to a display 58 for displaying images.

During operation, the control circuitry 32 may be designed to cause ultrasonic transducer 28 to vibrate. The ultrasound wave, represented by line 60 in FIG. 2, will propagate through the fluid, e.g. blood, fluid, or tissue surrounding the distal end 26 . A portion of the ultrasound wave so transmitted will be reflected back from both the moving structures such as valves and red blood cells, as well as from insonated structures to impinge on the transducer 28.

Because of the piezoelectric nature of the transducer, an electrical signal is thereby generated and transmitted by the cable 50 to the input of transceiver 48. A signal may then be variably transmitted to the Doppler circuitry 52 which may use a conventional amplifying and filtering circuitry commonly used in Doppler flow metering equipment. The Doppler circuitry 52 analyzes the Doppler shift between the transmitted frequency and the receive frequency to thereby derive an output proportional to velocity or other phenomena. This output may then be displayed at the display 54. The display 54 may be a suitable analog or digital display terminal. Accordingly, the user will be able to obtain a readout of velocity, blood rates hemodynamic or physiologic information.

In order to obtain fundamental imaging information, the control circuitry 32 triggers ultrasonic transducer 28 via the transceiver 48 to vibrate and produce an ultrasound wave. Once again, a portion of the wave or energy will be reflected back to the ultrasonic transducer 28 by the body features. A corresponding signal will then be sent by the cable 50 to the transceiver circuitry 48. A corresponding signal is then sent to the imaging circuitry 56 which will analyze the incoming signal to provide to the display 58. The display 58 may be any type of suitable display apparatus for displaying an image (fundamental or parametric) of the underfluid features.

The imaging can occur at anytime even while a therapeutic or surgical device is used at the distal end 26 of the catheter 20 within the field of view provided by the ultrasonic transducer 28. Accordingly, the user will be able to monitor his/her actions and the result thereof.

Further in FIG. 3, the catheter body 22 may include proximate to its proximal end 24 a suitable mounting structure 62 to the access port 40. A therapeutic or surgical device access 64 may be suitably attached to the structure 62 by suitable means, e.g., threaded, etc. As illustrated, an elongated cable-like member 66 will extend along the access port 40 and slightly beyond the distal end 26 of the catheter body 22 wherein the device 42 may be interconnected.

Figure 4:
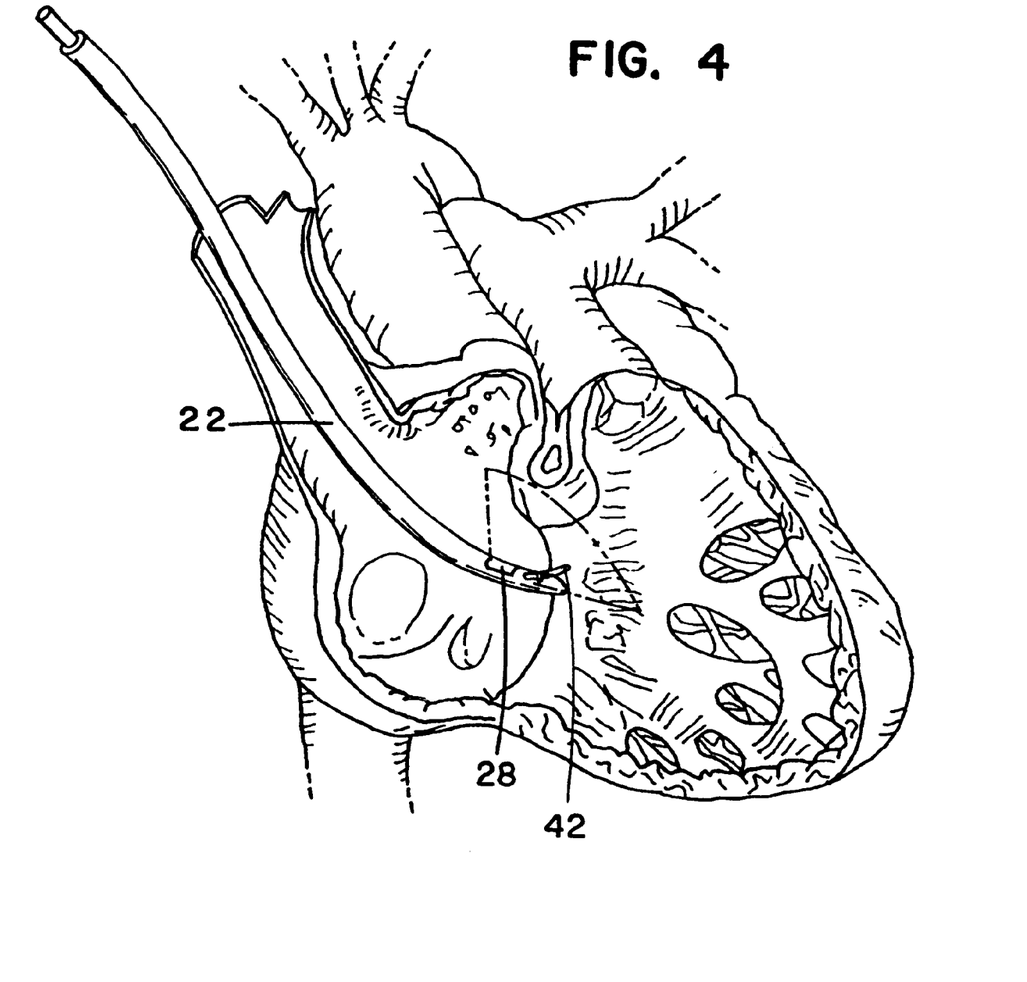
FIG. 4 is a perspective view of one embodiment of the underfluid ultrasound parametric imaging catheter apparatus in an underfluid environment in accordance with the principles of the present invention.

FIG. 4 shows that the parametric imaging ultrasound transducer catheter 30 can be inserted into an underfluid environment. The parametric images of a selected parameter or mode representing the underfluid environment can be viewed on the displays. In this embodiment, the therapeutic device 42 is inserted into the catheter access port 40 and operated in the field of view of the transducer 28. It is appreciated that the catheter 20 can also be a merely imaging catheter which may not include the access port 40 or guide wire port 44, or accommodate a device 42 or guide wire 46.

Also in FIG. 3, parametric information can be obtained or generated in numerous places in the acquisition circuitry. One can use the Doppler information from the Doppler Circuitry 52 and create parametric information and image via a parametric imager 68. This can be analog or digital information but considerably far down the image processing cascade and image circuitry. One can also create parametric information and images via a parametric imager 70 off of the imaging circuitry 56. This would include display of motion and gross anatomic information. A more mature parametric solution and image via a parametric imager 72 or 84 can be obtained from radio frequency (RF) data taken off of the beam former 76. The parametric information and resulting images at imager 72 is created by received data from the transducer 28 and is taken off very early in the image processing cascade, for example, just after the beam former 76. The digital information or data 78 is presented as parameterized image pixels of quantifiable information. The distribution of features (i.e., surrogate families of pixels) can be displayed 90 as the parametric image. Similarly, parametric information and image can be generated further along the imaging process chain, for example, after performing a scan conversion 80 and generating a digital data set 82. The digital data set 82 is used to generate a parametric image via a parametric imager 84. Accordingly, parametric imaging is a particular data processing solution that looks at distributions of paramaterized events and presents those real or mathematically derived distributions as a quantifiable geometric image. A parametric image can be a distribution of an image feature, a distribution of Doppler phenomena, a distribution of parameterized digital data pixels, or a distribution of post-scan conversion display information.

The use of an underfluid ultrasound catheter to generate parametric images via imagers 68, 70, 72, and 84 is unique. Parametric imaging is defined as the imaging of "parameters" which are visible two-dimensional, three-dimensional, fourth-dimensional, or non-visible higher-dimensional temporal events. Visible fourth-dimensional events include features such as cardiac contraction, valve leaflet motion, dynamic features, etc. Non-visible motion may include slow non-visible events (i.e., remodeling, aging, healing, etc.) or fast non-visible events (i.e., contractility, electricity, strain, compliance, perfusion, etc.) Parametric imaging requires: 1) an acquisition device (i.e., ultrasound machine and transducer); 2) rapidly or temporally sequenced acquired analog, digitized, or digital information; 3) a state-of-the-art "information" computer processor (quantum mechanical solutions); 4) a geometric presentation of the resultant parameterized information; and 5) a quantitative interactive display. It is appreciated that various types of acquisition techniques can be used. The techniques vary in sophistication (anatomic to digital pixel parameterization), modality (image, Doppler, phenomena etc.), information (analog, digitized, digital), and purpose (aging which is a slow event recording; electricity which is a very rapid nonvisible event; contractility which is a visible motion event). Specific examples of the applications will be discussed below.

A parametric imager selects at least one parameter of an event and generates an image which is a quantifiable geometric surrogate of a visible or non-visible event displayed in a comprehensible realistic manner. Quantified distributions of parameters represent a new and unique means for an underfluid catheter to appreciate phenomena such as dynamic physiology. Accordingly, a parametric imaging empowered ultrasound catheter, in addition to conventional imaging solutions, function, dynamic flow and hemodynamics, can obtain dynamic quantifiable feature extracted information from the insonated environment and display this information as a static or dynamic geometric figures from which discrete or gross quantifiable information can be obtained.

A parametric image is an image that acquires parameterized (i.e., mathematical variable) information either as gross features or increasingly fractionated discrete elements (pixels). The feature or element is parameterized (i.e., numerically weighed) and looked upon as a quanta of the event. The parameterized features or elements have distinguishing magnitudes. Groups of units (quanta or pixels or characteristic elements) are visible and can be continuously changing both in value and spatial distribution.

Any evolving or spreading phenomenon has a spatial distribution and volume and includes a sequence of changing geometric moments or "snapshots" of itself. The instantaneous "snapshots" or versions of an event collectively are perceived as a continuous and moving phenomena (i.e., heat) or object (i.e., contraction of the heart). Any moving or changing phenomenon is thus capable of being depicted as a sequence of geometric moments. Sophisticated computer acquisition devices can be configured to rapidly acquire dynamic physiologic information. The ultimate device is a form of quantum computation. The families of physiologic events or features are geometrically displayed. Thus, such events are visually and quantitatively explained, and ultimately why something happened by invoking the flow of time is described. Quantum descriptions of distributions resolve events into measurable units of simplicity and comprehensibility and can be looked upon as high-level simplicity derived from low-level complexity.

Described below are a few general examples of parametric images which can be obtained with the ultrasound imaging catheter. The present invention generally pertains to the introduction of parametric imaging to an ultrasound catheter. These examples represent only a sampling of an infinite array of parametric solutions. The present invention provides an ultrasound imaging catheter empowered with parametric solutions described herein. Parametric imagery is equated with the geometric (i.e., volumetric) display of physiologic events which is particularly unique and suited to the underfluid ultrasound tipped catheter. It is appreciated that the utilization and understanding of multidimensional quantifiable distribution of parametric events with the confines of fluid filled spaces have important clinical utility and implications.

Examples of multidimensional medical parametric imaging are described below, whereby visible or non-visible motion is recorded and quantified, and events mathematically expressed in numerous ways, depending on the clinical purposes. Parametric solutions are a unique introduction to ultrasound and never described in conjunction with a catheter system.

1) Change or Transformation

Normal and abnormal physiologic events which occur over time can be as slow as aging and remodeling or as rapid as the heart's myocardial contraction. Although one can perceive the evolution of the actual event, one cannot capture prolonged or instantaneous change as a separate phenomenon. At any moment in time, the phenomenon's change is so minute or transient that it cannot be separated as a distinct happening. The human senses perceive such events only as linear or cyclical continua. However, the computer is used to change or transform and express this phenomenon as a sequence of geometric moments. Change or transformation information is presented in a number of meaningful ways. For example, the volumetric excursion of a surface is presented as a geometric picture and measured as expression of the magnitude of change. The phenomenon change is expressed as an image and not the physical motion such as a wall contraction. In this circumstance, excursion is itself and not the wall surface, and motion is expressed as a volumetric expression of that which has changed or transformed.

Unique to the ultrasound expression of parametric images of the present invention is the manner in which the phenomenon is expressed. For example, electrical events are expressed as the instantaneous and sequential contraction of muscle fibers, transformation as a volumetric expression of that which has expanded or contracted or the mass which has changed, profusion as a feature of the insonated milieu, pressure as Doppler frequency shift, and metabolism as alterations in stiffness, etc. In each instance, the parametric solution is very much different from that described by CT, MR, or nuclear for that fact in any previous science. Further, the manner of display is uniquely differentiated in that it is the phenomenon of which is displayed in preference to the fundamental image. The phenomenon becomes the primary visible and quantifiable result. The resultant images, which are an expression of the event but not the structure, may have little resemblance to the original structure but will contain qualitative (visual) and quantifiable (mathematical) information important to the better understanding of the event.

2) Flow

The continuous movement of gas or liquid is normally invisible because of the rapidity of the event and the invisible nature of the perfusate. Doppler ultrasound can display blood flow as a shift in ultrasound frequency and displayed as a distribution event. Parametric expressions of flow capture multiple parameterized morphological and physiological phenomena, such as: 1) the space in which the event occurs, 2) the actual three-dimensional distribution of the event within the ultrasound space, and 3) quantifiable physiology of the fluid, such as velocity, viscosity, turbulence, etc. Parametric imaging takes an advantage of unique and powerful attributes of simultaneous visualization of quantifiable features, pixels, as well as the visualization of multiple phenomena (multi-parametric image) or information from multiple technologies (i.e., multi-modality parametric image).

3) Perfusion

Ultrasound parametric image of perfusion is expressed as a distribution of refractile feature changes caused by the interaction of ultrasound and a blood tracer such as spheres of gas. This is a quantifiable two- or three-dimensional surrogate distribution of the perfusate. A multi-parametric ultrasound would display multiple simultaneous events, such as function (transformation) and perfusion, simultaneously. The quantitative distribution of feature, such as flow velocity, can be utilized as an expression of the magnitude of a perfusion/function defect or burden.

4) Pressure

Pressure can be perceived but not visualized without enhancement. The multi-dimensional display of pressure (i.e., volumetric distribution of quantifiable features or families of parameterized pixels) processes otherwise non-visible phenomena into a visible format. In the new imaging paradigm, instantaneous pressure, such as recorded ultrasound Doppler velocity shift, can be displayed as a three-dimensional distribution. An ultrasound surrogate of a dynamic pressure map betters the highlights of regional and global physiological dynamics. The uniqueness of the parametric solution is the volumetric display of quantifiable physiology. Pressure itself becomes the picture.

5) Contractility

Distribution of velocity, force, and traction parameters, such as fractional shortening, and distribution of contractile phenomena, can be displayed in a volumetric image. The parameterized phenomena, and not the normal ultrasound signal, is itself the primary image. Ultrasound tissue Doppler velocity imaging (TDI-velocity) and motion imaging record the velocity and succession of muscle contraction, respectively. A volumetric image of these events, displayed as a geometric image, displays normal and abnormal functional activity of the heart in a visual and quantifiable manner. The resultant parametric solution may have little resemblance to the original fundamental information, such as TDI-velocity, but imparts more meaning by being presented as a quantifiable volume.

6) Image Features

Tissue texture metrics (i.e., features) can be assessed in many ways. The parametric imaging solution can actually elucidate dynamic tissue histopathology. When displayed as a higher dimensional parametric image, normal and abnormal tissue can be separated from its surroundings. Feature extraction is a quantum statistical technique, which can analyze the entire volume which can be used to create a new image of the organ represented by one or more of its embedded characteristics. This parametric image is unique to the underfluid catheter systems.

7) Electricity

Electrical forces are invisible events to ultrasound. However, surrogate phenomena can be detected and recorded using ultrasound technology (for example, tissue Doppler imaging velocity or acceleration which parameterizes the sequence of myocardial muscle contraction during electrical depolarization and repolarization). When processed into a visible map and displayed as a volumetric image, a volumetric parametric image is created. This image is a surrogate of electrical depolarization but unlike the actual mapping of electrical events, as conventionally occurs, a surrogate ultrasound parametric solution is utilized. Visualization of the sequence of polarization and depolarization displayed as a distribution in these cases allows better understanding of normal and abnormal electrophysiology. Such understanding can be used to direct therapy of arrhythmias as currently practiced in an electrophysiologic laboratory. Quantifiable alterations of the geometry of the electrical field have therapeutic implications. This parametric solution is unique to the underfluid ultrasound systems.

8) Metabolism

Metabolic activity and change of underlying function are not visible to the normal human senses. However, through various higher-dimensional displays of ultrasound acquisition techniques, metabolic activity is modeled, accurately depicted, and most importantly expressed as distributions of variable metabolic activity, such as myocardial injury, death, or hibernation.

9) Others

It is appreciated that there are an infinite number of higher-dimensional parametric ultrasound solutions.

Figure 5:
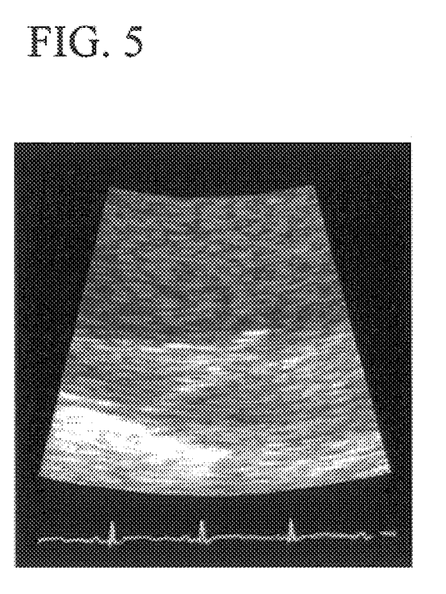
FIG. 5 is an image display of a segment of left ventricular myocardium using a phased array ultrasound imaging catheter without applying a parametric image solution.
Figure 6:
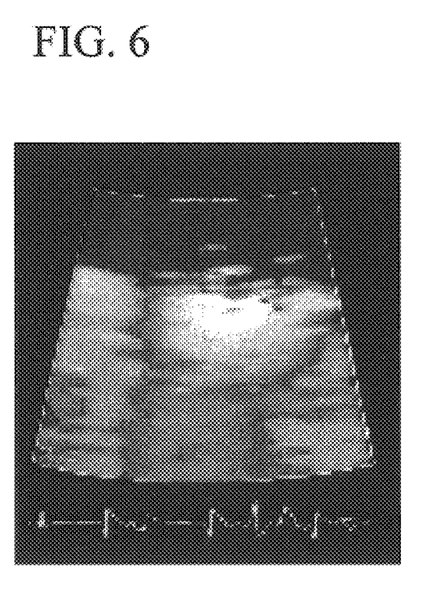
FIG. 6 is an image display of a velocity mode of the segment of left ventricular myocardial (i.e., the parameter is the velocity and is displayed as a surrogate of electricity and the depolarization/contraction of the myocardium) using a phased array ultrasound imaging catheter applying the parametric image solution in accordance with the principles of the present invention.

As an example, FIG. 5 shows an image display of a segment of left ventricular myocardium using a phased array ultrasound imaging catheter without applying a parametric solution and represents the fundamental image. The frequency of the transducer is 7.5 MHz and the diameter of the catheter body is 10 French (one French divided by Pi equals one millimeter (mm)). FIG. 6 shows the same myocardium displayed as a parametric myocardial velocity map. Each pixel and family of like velocity pixels appear as concentric evolving contractual waves. Parameterized features include velocity, distribution, volume, and variable concentric waves of velocity. The ultrasound tipped catheter is used for parametric imaging in accordance with the principles of the present invention. As shown in FIG. 6, the myocardial segment is imaged with parametric tissue Doppler (TD) at a frame rate of >=100 frames per second and reformatted to a temporal sequence which is more familiar to the human reality (i.e., static or visible wavelets of surrogate electrical phenomenon). Using the velocity mode of TD, regional myocardial contraction is parameterized to equate to an electrical event (i.e., the ultrasound visualization of electricity using surrogate pictures of tissue acceleration velocity). Each segment of muscle is given a color based on recorded regional pixel velocity. Each pixel has a specific value related to velocity, all similar velocities have a similar color. As shown, the initial and now slowing velocity is the epicenter of the electrical stimulus (bright green). The contractile velocity spreads outward in wavelets from the epicenter, velocities spread outward like waves in a pond with each wavelet having a similar instantaneous velocity (orange, deep red, blue). The initial point of electrical excitation is visually and quantifiably localized to the point of the initial muscle contraction. Propagation of the electrical surrogate is the realistically and quantitatively assessed. Such a parametric image is unique to underfluid ultrasound systems. As shown in FIG. 6, the image is a two-dimensional surrogate display designed to show an electrical epicenter. The phenomenon, however, is multidimensional and distributes irregularly. Other multidimensional displays of this event are intuitive and would be designed to answer specific physiologic questions.

Figure 7:
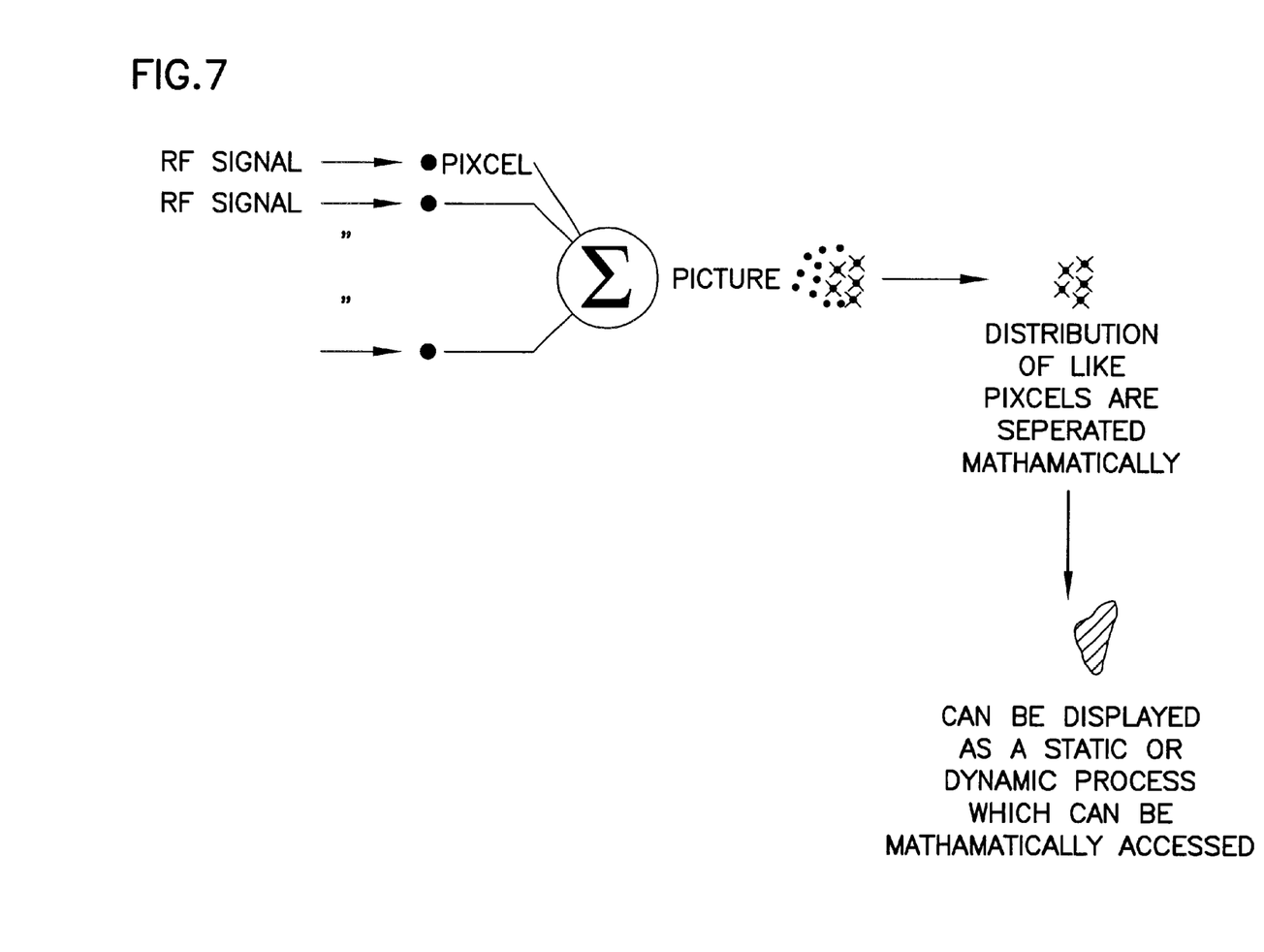
FIG. 7 is a schematic view of one example of presentation and display of radio frequency (RF) signals in a parametric imaging process in accordance with the principles of the present invention.

FIG. 7 illustrates a schematic view of one example of presentation and display of radio frequency (RF) signals in a parametric imaging process in accordance with the principles of the present invention. The RF signals are parameterized and presented as quantifiable pixels of image information. The pixels are then summed to form a fundamental picture or image. The parameterized pixels contain mathematical features of families of pixels which can be separated into meaningful parametric distributions and displayed as a new geometric image. These new images can be presented as geometric moments or dynamic cyclical or continues events. The new image often does not appear like the fundamental image or have an intuitively familiar analogy or analog. However, the new image is a simple quantifiable geometric figure of an otherwise complex event.

Figure 8:
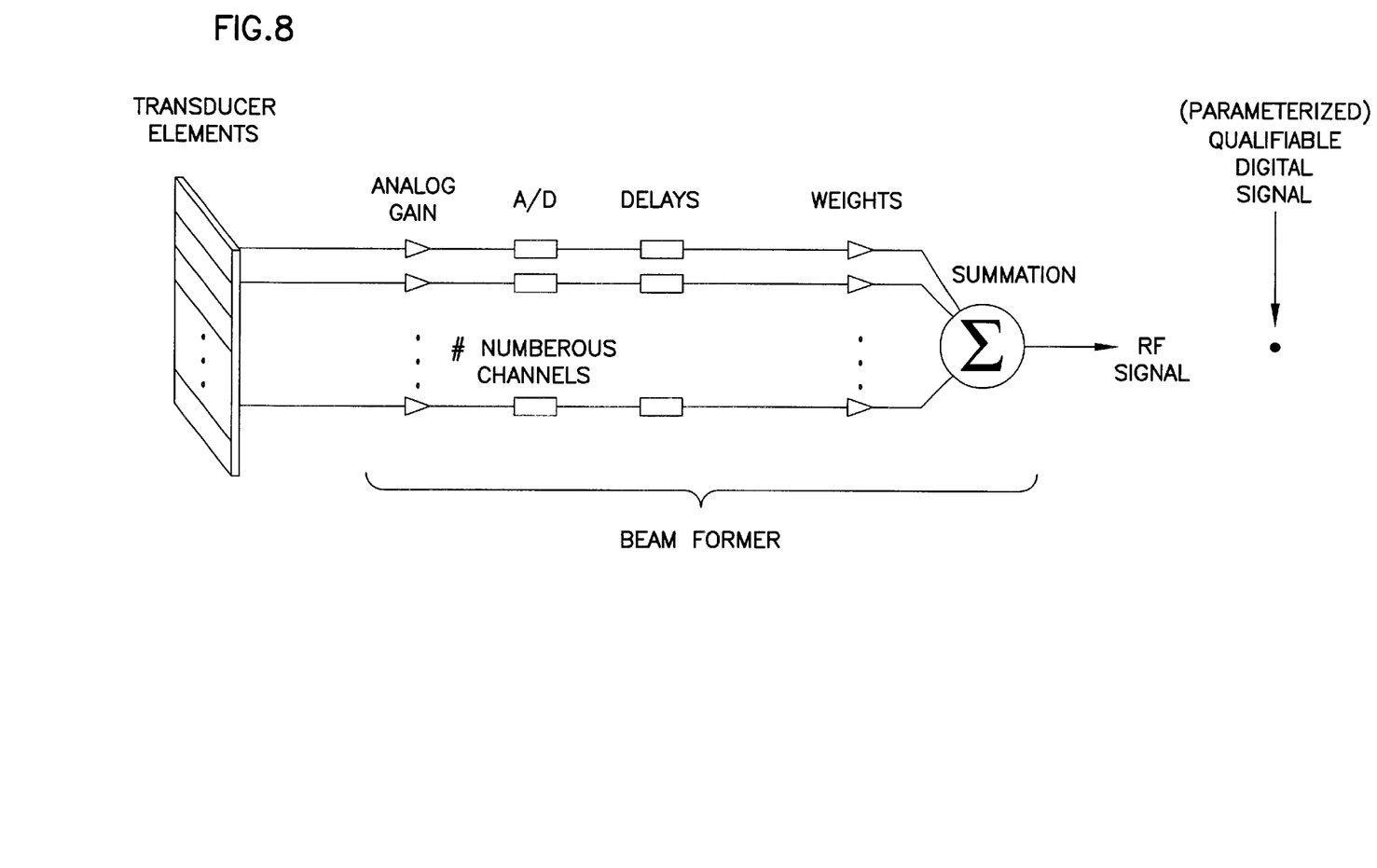
FIG. 8 is a schematic view of one example of acquisition of transducer received signals and formation of the RF signals in the parametric imaging process in accordance with the principles of the present invention.

FIG. 8 is a schematic view of one example of a sophisticated acquisition of transducer received signals and formation of the RF signals which are parameterized in accordance with the principle of the present invention. The RF signals are the output of the beam former 76 (FIG. 3). The received signals from the transducer elements are amplified (e.g. analog gain) to ensure the optimal use of the dynamic range of the analog-to-digital (A/D) converters. The analog gain factor varies according to the distance the received signals travel into the insonated tissues, i.e., deep signals are amplified more. The signals are then delayed individually to focus the beam to account for certain depth and direction. The delayed signals are weighed to obtain the desired apodization and beam profile. The weighed and delayed signals are summed in phase to result in RF signals. The RF signals are digital, thus are more easily parameterized, and thus are most suited to the parametric solution.

Figure 9:
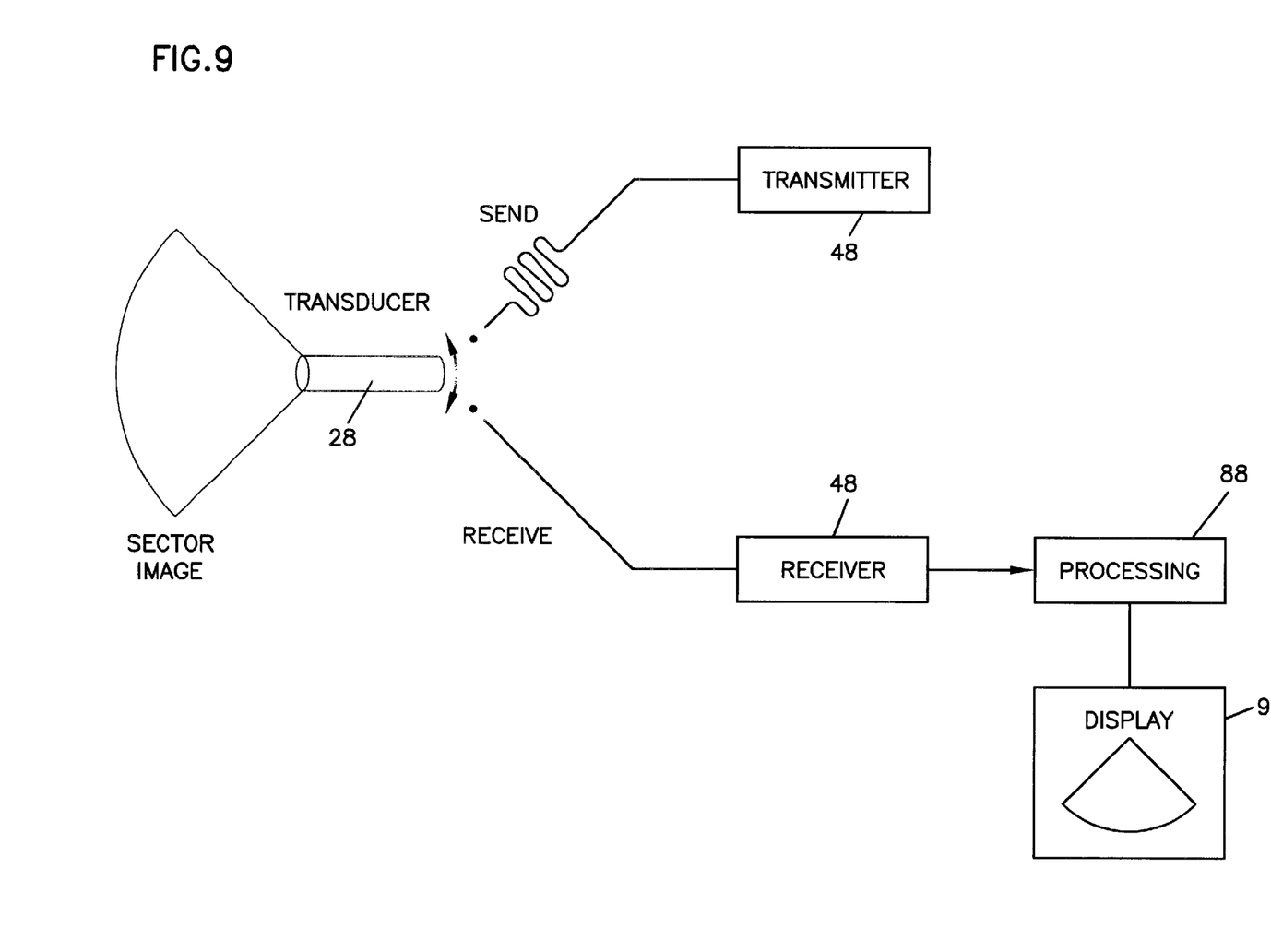
FIG. 9 is a schematic view of a parametric imaging catheter apparatus in accordance with the principles of the present invention.

FIG. 9 illustrates a schematic view of one example of parametric imaging catheter apparatus in accordance with the principles of the present invention. The transmitter 48 sends signals to the transducer 28 which transmits signals to an underfluid structure (FIG. 4) and in turn receives echo signals from the structure. The received signals are then sent to the receiver 48 to be processed in the processing device 88 (FIG. 3) and to be displayed by a display 90. It is appreciated that the processing device 88 may also incorporate with the processing device 86 as shown in FIG. 3 to obtain parametric imagers from the Doppler circuitry 52 and/or imaging circuitry 56.

It is appreciated that the configuration and arrangement of the catheter and catheter body itself can be varied within the scope and spirit of the present invention. The present invention deals with the use of parametric imaging in such catheters in order to uniquely assess dynamic natural events such as physiology. The parametric imaging catheter apparatus of the present invention is capable of visualizing visible as well as very fast or very slow non-visible motion events and is capable of creating measurable geometric surrogate representations of physiology, including transformation, blood flow velocity, perfusion, pressure, contractility, image features, electricity, metabolism, and a vast number of other constantly changing parameters. Parametric solutions have not been applied to a catheter system. The present invention allows presentation of physiologic phenomena as easily understood geometric images temporally and realistically reformatted to the human's two-, three-, and four-dimensional comprehension of reality.

In one preferred embodiment, the ultrasonic transducer 28 preferably has a frequency of 5 to 30 megahertz (MHz) and more preferably a frequency of 5 to 12 MHz, and furthermore preferably a frequency of 7.5 MHz. The catheter body 22 has preferably a diameter of 4 to 15 French (one French divided by Pi equals one millimeter (mm)) and more preferably a diameter of 5 to 10 French, and further more preferably a diameter of 8 to 10 French (2.6 to 3.2 mm diameter). The optional access port 40 has preferably a diameter of 7 to 8 French, and the guide wire port 44 has preferably a diameter of 0.025 to 0.038 inches. It is appreciated that the ultrasound tipped catheter may or may not have other features such as articulation capability, and may or may not have a port (guide wire port and/or therapeutic device assess port). The catheter is capable of performing various acquisition technologies such as harmonic imaging, pulse inversion, intermittent imaging, automated edge and cavity delineation, etc. The present invention is unique firstly as it pertains to a catheter system, particularly to an underfluid ultrasound catheter, and secondly, the present invention pertains to a parametric image solution.

It is also appreciated that the transducer 28 may have variable configurations and arrangements, such as longitudinal, toroidal (longitudinal rotation), forward-and-side viewing, volumetric (3-Dimensional viewing), mechanically rotating element(s), etc.

It is further appreciated that the catheter 20 may have full Doppler capabilities which includes pulsed and continuous wave Doppler, color flow Doppler, tissue Doppler (velocity, acceleration, and power modes), strain-rate, etc.

The present invention pertains to the incorporation of a unique imaging solution (parametric imaging) into an ultrasound tipped catheter. Parametric imaging is an evolving concept based on an evolving technology empowered by increasingly sophisticated computer management of acquired information. For the purposes of this imaging technique, information is broken down into measurable features or into small measurable components and likened to quanta (i.e., elemental units). Parameterization requires a digital or digitized image presentation (i.e., an image comprised of mathematically measurable components). The change over time of the elemental feature or unit can be measured (i.e., velocity, strain-rate, etc.). Features and/or units, on a larger scale, are envisioned as having definable meaningful characteristics, which when presented as a group, are interpreted as a surrogate of a physiological events, such as: (infarct, perfusion, electricity, transformation, etc.). An event can be defined as having a measurable distribution (i.e., volume, mass, surface), as well as a variable mathematical value of the constant constituent pixels (i.e., quanta). The distribution of the event is typically unpredictable and irregular and best defined by a multi-dimensional image presentation (i.e., more meaningful and understandable to the observer as the dimensional presentation increases from a two- to three- to four-dimensional presentation). The incorporation of a parametric solution into an underfluid catheter in particular does not exclusively foster the visualization and quantitation of physiologic and feature characteristics of the insonated volume.

The computer interfaced image processing may include the use of any quantifiable acquisition technique including: harmonics, Doppler, pulse inversion, etc., which capture motion as discrete quantifiable local events or distributions of events. One of the unique aspects of the present invention is the display of that information and not the specific acquisition transducer or information acquisition algorithm.

The computer interfaced image processing optimally includes the capture of motion (fourth- and higher-dimensional events). The examples of physiologic motion are as follows: fast invisible motion (i.e., higher-dimensional information, for example, electricity, strain, elasticity, pressure, force, perfusion, etc.); slow invisible motion (i.e., higher-dimensional information, for example, aging, remodeling, transformation, etc.); and visible motion (i.e., fourth-dimension, for example, contractility, translated motion, valve motion, etc.). One unique aspect of the present invention is the assessment of these events by the use of surrogate information presented as quantifiable units (pixels, quanta) and displayed as quantifiable spatial distributions (surface, area, volume). For example, fast invisible electrical events are in one embodiment displayed as tissue Doppler acceleration and the temporal and spatial distribution of that surrogate event; slow invisible motion of remodeling is displayed as a geometric distribution of the phenomenon of quantifiable change while tissue itself is not displayed subservient to the image; and the visible motion of contractility displayed as quantifiable volumetric excursion.

The computer interfaced image processing further includes the captured otherwise invisible features (i.e., feature extraction). The examples are as follows: microanatomy including fibrosis, edema, infarction, etc., and perfusion including microcirculation (echo contrast, Doppler blood cell tracking, target tracking, etc.). It is acknowledged that the particular acquisition technique, expressed mathematical events, particular phenomenon recorded are merely exemplary of the present invention. In general, the present invention relates to a new quantifiable image solution (i.e., parametric imaging) applied specifically to any ultrasound catheter device used for underblood or fluid application.

The geometric presentation of physiologic events includes: a) Distribution of quanta: motion events are presented as quantifiable distributions; b) Scalable dimensions: one-dimensional, two-dimensional, three-dimensional, four-dimensional and higher-dimensional presentations. (Higher-dimensional events are invisible to the human senses and are normally perceived as continuous events, e.g., temperature, electricity, aging, etc.).

The quantum mathematics and quantum computing includes: a) Mathematics of quanta, examples of quanta include electricity, pressure, sound; b) Quantum math where location and velocity typically cannot be computed simultaneously; c) Geometric presentation of physiologic events and otherwise unseen features; and d) The use of probability theory (fractal geometry, chaos, fuzzy, logic . . . mathematics which presents highly accurate predictions of natural events).

It is to be understood that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A catheter apparatus capable of parametric imaging an underfluid structure, comprising:
   a catheter body;
   a transducer, disposed on the catheter body, receiving signals which represent an event of at least one selected parameter, and
   a parametric imager configured and adapted to process the signals and presenting at least one selected parameter of the event in an image, the event cable of being a non-visible multi-dimensional event which is non-visible to a human user's eye prior to the processing by the parametric imager,
   wherein the parametric imager is configured and adapted to processe the signals to form RF signals, the RF signals being digital signals and parameterized to present at least one selected parameter of the event in the image.

2. A catheter apparatus in accordance with claim 1, wherein the image is a two-dimensional image.

3. A catheter apparatus in accordance with claim 1, wherein the image is a three-dimensional image.

4. A catheter apparatus in accordance with claim 1, wherein the image is a four-dimensional image.

5. A catheter apparatus in accordance with claim 1, wherein the image is a higher-than four-dimensional image.

6. A catheter apparatus capable of parametric imaging an underfluid structure, comprising;
   a catheter body;
   an ultrasonic transducer, disposed on the catheter body, receiving ultrasonic signals, the ultrasonic signals representing an event of at least one selected parameter; and
   a parametric imager configured and adapted to process the ultrasonic signals and presenting at least one selected parameter of the event in an image, the event capable of being a non-visible multi-dimensional event which is non-visible to a human user's eye prior to the processing by the parametric imager,
   wherein the parametric imager is configured and adapted to process the ultrasonic signals to form RF signals, the RF signals being digital signals and parameterized to present at least one selected parameter of the event in the image.

7. A catheter apparatus in accordance with claim 6, wherein the image is a two-dimensional image.

8. A catheter apparatus in accordance with claim 6, wherein the image is a three-dimensional image.

9. A catheter apparatus in accordance with claim 6, wherein the image is a four-dimensional image.

10. A catheter apparatus in accordance with claim 6, wherein the image is a higher-than four-dimensional image.

11. A catheter apparatusapparatus capable of parametric imaging an underfluid structure, comprising:
    an elongated body having a longitudinal axis;
    an ultrasonic transducer array having at least one row of ultrasonic transducer elements mounted on the body, each of the ultrasonic transducer elements of the array being concurrently operated as a part of the array for transmitting ultrasonic signals, the ultrasonic signals representing an event of at least one selected parameter;
    a parametric imager configured and adapted to process the ultrasonic signals and presenting at least one selected parameter of the event in an image, the event capable of being a non-visible multi-dimensional event which is non-visible to a human user's eye prior to the processing by the parametric imager; and
    an electrical conductor disposed in the body for electrically connecting the array to a control circuitry,
    wherein the parametric imager is configured and adapted to process the ultrasonic signals to form RF signals, the RF signals being digital signals and parameterized to present at least one selected parameter of the event in the image.

12. A parametric imaging ultrasound underfluid catheter, comprising:
    means for digitizing signals representing one selected parameter of an event;
    means for quantifying the signals representing one selected parameter of the event in an image, the quantifying means operatively connected to the digitizing means; and
    means for presenting a geometric image of the event, the presenting means operatively connected to the quantifying means and the digitizing means,
    wherein the digitizing means is configured and adapted to process the signals to form RF signals.

* * * * *